United States Patent [19]

Aladjem et al.

[11] Patent Number: 4,554,257

[45] Date of Patent: Nov. 19, 1985

[54] ASSAYING IMMUNOREACTIVE AND LIKE SUBSTANCES BY MEASUREMENT OF AGGREGATE CLASSES

[76] Inventors: Frederick J. Aladjem; Padmasini K. Ayengar, both of 845 Las Palmas Rd., Pasadena, Calif. 91102

[21] Appl. No.: 489,734

[22] Filed: Apr. 29, 1983

[51] Int. Cl.$^4$ ........................ G01N 33/54; G01N 35/00
[52] U.S. Cl. .................................... 436/519; 250/574; 356/341; 436/517; 436/533; 436/534; 436/805; 436/807; 436/827
[58] Field of Search ........................ 250/574; 356/341; 436/517, 533, 534, 805, 807, 827, 519

[56] References Cited

U.S. PATENT DOCUMENTS

| | | | |
|---|---|---|---|
| 4,157,871 | 6/1979 | Anderson | 436/805 X |
| 4,203,724 | 5/1980 | Sawai | 436/805 X |
| 4,305,665 | 12/1981 | Achter | 356/339 |
| 4,446,239 | 5/1984 | Tsuji | 436/532 |

OTHER PUBLICATIONS

Chemical Abstracts, 96: 100539h (1982).

*Primary Examiner*—Sidney Marantz
*Attorney, Agent, or Firm*—Charlton M. Lewis

[57] ABSTRACT

The disclosed methods improve conventional agglutination processes for assaying immunoreactive and like substances, primarily by improving the measurement of the agglutination itself. Suspensions containing agglutinated particles are automatically inspected, preferably intermittently during the agglutinating reaction, and the resulting data are processed to identify individual particle aggregates of a selected limited class, which may, for example, comprise aggregates having sizes within a limited size interval. The numbers of such aggregates are compared with corresponding reference values obtained with standard solutions and suitable controls to evaluate the concentration of one of the reactive substances, or other information. The aggregate size intervals and other parameters which are used to define aggregate classes are preferably selected with attention to the detailed behavior of each test system.

53 Claims, No Drawings

ASSAYING IMMUNOREACTIVE AND LIKE SUBSTANCES BY MEASUREMENT OF AGGREGATE CLASSES

OUTLINE OF THE INVENTION

This invention provides improved methods for measuring the extent of agglutination of insoluble particles due to reaction of immunoreactive and like substances, at least one of which is present on the particles. The carrier particles may be artificial, as latex beads, or may be natural, as blood or tissue cells or microorganisms.

More particularly, the invention provides counts of individual aggregates limited to one or more specified classes. An aggregate class may, for example, comprise all aggregates having sizes with in a discrete selected size interval, or scattering light within a discrete selected interval of intensity as determined by measurement of each individual aggregate. Such counts are preferably measured at a series of times. The resulting relatively detailed knowledge of the patterns of development of the aggregates permits the extent of agglutination to be determined with improved scope and accuracy.

Moreover, for a given system, it is usually possible to select particularly favorable classes of aggregates for measurement, together with an especially appropriate time for enumerating the aggregates of each class, such that the resulting aggregate counts reflect especially sensitively the overall extent of agglutination.

A further aspect of the invention involves use of such measurements of the extent of agglutination for improved assay of immunoreactive and like substances in test solutions or suspensions by processes employing agglutination of insoluble particles. Many conventional processes are well known for obtaining at least approximate assay of the concentration of such test substances by comparing the extent of agglutination due to reaction of the test substance with corresponding reference data obtained with standard reactants. By permitting improved measurement of the agglutination itself, the invention directly enables all those conventional assay processes to be made correspondingly more accurate and reliable.

Further than that, the invention preferably derives the concentration of a test substance from counts of individual aggregates of only one or more selected classes, rather than from an averaged distribution of all aggregates, as has been typical of the prior art. The particular class or classes of aggregates to which the measurements are responsive are typically selected individually for each test system, and especially for the particular test substance to be assayed. The primary criterion for that selection is preferably that the measured counts of the selected aggregate classes be especially well correlated with the concentration of the analyte. The invention thus eliminates from consideration all measurements that are less well correlated with the value to be determined than those obtained using the specific class or classes selected.

The class of aggregates to be included in the assay of a particular analyte may be distinguished in many different ways. The selected aggregates are typically characterized by a defined range of values of an aggregate parameter. Such a parameter is then distinctive of the class in the sense that measurement or calculation of the parameter value for any individual distinguishes whether or not that aggregate belongs to the class.

Such class defining parameter values for individual aggregates are generally obtained from the results of optical, electrical or mechanical measurements, or combinations of these. Examples of optical parameters include the scattering coefficients, absorbance or reflectance, the total optical density and the refractive index. Electrical parameters include the electrical charge carried by individual aggregates, impedance and conductance. Parameters that are configurational in nature, such as the size and shape of individual aggregates, are obtainable in principle by mechanical measurements, but are usually measured most conveniently by optical means. Such parameters may be measured for individual aggregates, for example, by optically scanning a representative field of the aggregate suspension to develop signals representing light intensity at many closely spaced positions, and analyzing the resulting signals with the aid of a computer, as more fully described below. Density can be measured in terms of the rate of settling of individual aggregates. It will be realized that many measurement results and the corresponding or derived class parameters will be obtained by a combination of techniques.

A particularly effective parameter by which to distinguish the class of aggregates to be included in the assay of a particular substance is the aggregate size. The patterns of development of aggregates having various specified sizes have been found to differ significantly from each other and from the development pattern obtained when all sizes of aggregates are lumped together, as is typical of the prior art. Thus, under any given set of operating conditions, a limited range of aggregate sizes can ordinarily be identified for which the number of aggregates having sizes within that range is an especially sensitive function of the initial concentration of the test substance under assay. Hence, by considering only (or primarily) aggregates in such a well correlated size range, or in several such ranges, and by measuring at times that are appropriate for the particular sizes measured, the accuracy and reliability of assay can be significantly increased over what was possible in the prior art. Similar discussion applies also to the development patterns and utility of limited aggregate classes defined in terms of parameters other than aggregate size.

In practice, the particular class or classes of aggregates selected to be measured, and the most effective measurement time or times for each class, are typically chosen with the aid of preliminary experiments with each reagent system. For example, several known reference concentrations of the test substance to be assayed are initially reacted with aliquots of a suitable complementary substance, one of said substances being typically present on surfaces of insoluble cells or other particles. The resulting aggregates are observed individually and their distribution is measured with respect to whatever parameter is considered a potential basis for defining a favorable aggregate class for assaying the test substance. Those distribution measurements are typically carried out for each concentration of the test substance, and are repeated at several times during the course of the reference reactions.

From the resulting data it is possible to ascertain the dependence of the selected aggregate parameter and number upon other parameters of the system, including especially the time of measurement and the initial reference concentration of the test substance. From that reference information, combinations of parameter values are typically identified for which the aggregate count varies especially sensitively, and is thus especially well correlated, with changes of concentration of the test substance. That count also preferably has a relatively stable value when considered as a function of each of the other parameters, including the time of measurement. Such identified parameter values define conditions of measurement that are particularly favorable for assaying the test substance in question.

As an example, measurement and analysis of the aggregate size distribution produced by the described reference reactions in a particular test system may demonstrate that a given difference between two values of the initial concentration of the test substance causes a change in the count of small aggregates that is greater than the change in the count of larger aggregates when measured during a relatively early time period; but that measurement of those same two sizes during a later time period reverses that relation. Under that illustrative condition, aggregates of the smaller size would form a more favorable class for measurement at the earlier time, and the larger size would be a more favorable class at the later time.

In addition to such criteria, preference may be given in selection of parameters to those values or value intervals, and the associated measurement time periods, for which the aggregate count depends upon the test substance concentration in a linear or other desired specific functional manner.

Exploration of the reference data typically also includes consideration of more complex functions that are derivable from the described aggregate counts and that may respond still more sensitively to variations of the test substance concentration. For example, the rate of change of the aggregate count for a specified range of an aggregate parameter can be computed from counts at multiple times. Also, such counts may be extrapolated to a time outside the range of actual measurement, such as "infinite time," for example, at which no further significant change occurs. By extending the field of investigation to such derived parameters the invention makes possible still higher correlation between the observed variable and the concentration to be assayed.

The general area of applicability of the new method of assay may be summarized as including the quantitation by methods including agglutination in mixtures of such diverse substances as drugs, low and high molecular weight hormones, plasma proteins, antibodies, cellular antigens and any material which can be detected by specific reactions leading to particle agglutination. Those reactions include antigen-antibody reactions, lectincarbodydrate reactions, receptor-ligand reactions, etc. One particularly useful field of application of the invention is the identification of natural particles by detection and quantitation of molecules or structures on their surfaces. Subjects to be so detected and quantitated may in general either occur naturally or be coupled artificially on the particle surfaces. General examples are cell typing, such as the typing of red blood cells prior to transfusions; the typing of white blood cells, for example to quantitate the various subpopulations of B-cells, T-cells and monocytes in the circulation of an individual's blood; and the identification of other natural cells, which may be single cells, as microorganisms, or groups of cells, as seeds and pollens.

In this connection, to overcome possible problems of steric hindrance and to obtain sufficient bridging between cells, it is often useful to use antibody or other complementary substance not in solution but coupled to small particles or to other cells, i.e., both reactants are present on the surfaces of particles.

The invention is not limited to use of the direct agglutination reactions, but also provides improved quantitation of reactants using each of the numerous modifications of the agglutination reaction, such as those requiring prior manipulation of reactants or addition of supplementary reactants. Such modifications include, for example, the Coombs process, procedures involving inhibition or enhancement of agglutination, and the coagglutination reaction.

In the present specification and claims the term antibody is intended in general to include where appropriate monoclonal antibody, antibody fragments possessing antigen binding activity, and artificially produced heteroligating antibody. Also, the term anti-antibody is intended in general to include where appropriate staphylococcal Protein A and like materials with anti-immunoglobulin activity.

The term particles is intended to include both natural and artificial particles. Examples of natural particles are blood or tissue cells, microorganisms and small naturally occurring groups of cells such as pollens and organelles. Artificial particles may be formed of any suitable material, such as latex or glass beads.

Further aspects of the invention will be described below.

BACKGROUND OF THE INVENTION

It is well known that the presence of reactions between antigens and their specific antibodies, or between other pairs of complementary substances which react specifically with each other, can be demonstrated by agglutination of insoluble particles to which one of the substances is bound. Such particles may be natural cells carrying specific receptors, antigens or antibodies, for example, or may comprise artificial "beads" of latex, glass or other suitable material. The beads are first sensitized by coating them, typically by adsorption or chemical bonding, with molecules of one reactive substance. When the sensitized cells or beads are contacted with a solution containing the complementary reactive substance, molecules of the two reactants become bound together. If the dissolved reactant has multiple valency the reaction may link the cells or beads together to form aggregates. Detection of such aggregates demonstrates presence of the reaction, and may indicate the types of reactants or receptors on the particles, or may provide a semi-quantitative measure of the concentration of the dissolved reactant.

Agglutination of cells by reaction with antibodies or the like is one of the oldest serologic procedures for the identification of bacteria and other microorganisms. It has also been widely used for blood typing and for cross matching. Such agglutination processes include variants such as indirect agglutination and inhibition of agglutination, in which additional steps are required to finally produce the agglutination that is to be measured. Such other steps typically include addition of reagents and washing, and usually follow the primary reaction of the original complementary reactants. Particle agglutination produced with the aid of such supplemental procedures is nevertheless considered to be "due to" that primary reaction, without which the supplemental procedures would be ineffective.

The present invention is applicable generally for assaying the extent of agglutination in connection with all known processes of the general type indicated above, as well as the numerous related processes derivable from them by obvious variations.

Cells or other particles may be coated, either naturally or artificially, with characteristic antigens or antibodies, and may then be caused to agglutinate by the appropriate complementary reagents. The literature includes many descriptions of the selection, preparation and/or sensitization of carrier particles to carry a wide variety of substances for reaction with specific complementary substances. Also well known are detailed procedures for carrying out such reactions to produce particle agglutination.

In general, carrier particles can be sensitized by coating with either an antigen or its complementary antibody, so that the process of agglutination can be used for assaying a test solution for either member of such a pair of complementary substances. The procedure is also applicable, with suitable selection of the carrier particles, to virtually any substance which is capable of combining with a complementary substance in a specific manner generally similar to the immunoreactions of antigens and antibodies. For example, lectins are known to react specifically with particular carbohydrates. Either member of such pairs can, in general, be associated with the particles, whether natural or artificial, and will tend to cause agglutination upon reaction with the complementary member. Such agglutination can be used to assay either member of the pair of reactants.

Many naturally occurring carrier particles, such as lymphocytes, other cells and bacteria, have characteristic binding sites and may be quantitated directly by use of appropriate antibodies or lectins which are specific to the sites and cause the particles to agglutinate. For example, many types of bacteria carry antigens that are characteristic of the particular type. Such bacteria may be caused to agglutinate when contacted with an antibody specific to the carried antigen. That reaction may be used for identifying bacteria by the resulting agglutination when contacted with an antibody known to be specific to the antigen; or may be used for demonstrating presence in a patient's serum, say, of antibodies against a particular type of bacteria by agglutination produced when such bacteria are added to a sample of the serum. A similar reaction is widely used for typing a patient's red blood cells by observing the type of antibody that reacts with them to produce agglutination.

Moreover, it is not a requirement that detectable aggregation occur when the test reactant to be assayed is brought into contact with the complementary substance; rather, combination of the two complementary reactants may occur without aggregation at that stage, and further manipulation or addition of reagents may be needed to produce the agglutination by which presence of the test reactant is to be assayed. Illustrative of such indirect agglutination processes is the Coombs test. For example, an original reaction between an antigen carried on natural or artificial particles and a dissolved antibody may bind the antibody but fail to produce apppreciable agglutination. Conventional additional steps to produce aggregation then may include elimination of dissolved non-reactive material from the particles and their coupled reactants, as by centrifugation and washing or by chromatography or other methods; followed by addition of a supplementary reactant complementary to the antibody, such as an anti-antibody, specific to the first antibody, produced in a suitable animal. The particle agglutination produced with the aid of such supplemental procedures provides a measure of the extent of the original immunological reaction, which may be used to assay either the antigen on the particles or the antibody.

A further type of assay by indirect agglutination depends upon the ability of certain substances to inhibit agglutination. Measurement of the extent of such inhibition may be used to determine the concentration of the inhibiting substance in a test solution. For example, agglutination due to reaction of an analyte bound to insoluble particles and a specific antibody in solution is typically inhibited by presence of dissolved molecules of the analyte. The dissolved analyte reacts with the antibody in competition with the bound analyte, decreasing the effective antibody concentration available for agglutinating reaction with the bound analyte.

In actual practice, in using inhibition for analyzing a test solution for an analyte, improved sensitivity is obtained by first allowing the test solution to react with a limited amount of dissolved antibody before adding the particles with the bound analyte. If the amount of antibody in that reaction is adjusted to produce slight but clearly detectable reference agglutination when there is no analyte in the test solution and hence no inhibition, even a trace of analyte in the test solution tends to cause a relatively large percentage decrease in that slight reference agglutination. Hence, with suitable precautions, the test can be made quite sensitive. The method is especially useful for quantitation of analytes such as low molecular weight hormones or drugs which occur usually in low concentrations in serum or other fluids.

The general method of inhibition of agglutination can be used to assay in a test solution either of the complementary substances provided the test substance can be attached to, or is present on suitable particles. As in agglutination generally, the particles may be natural or artificial.

The sensitivity and speed of assay by agglutination may often be enhanced by adding a hydrophilic but immunologically inactive material such as polyethylene glycol which tends to bind water. That places the particles in a more hydrophobic environment, enhancing their tendency to bind to each other.

Furthermore, depending upon the particular system, the sensitivity may be increased and non-specific reactivity decreased if, instead of whole antibody, only an antibody fragment is used for coupling to beads, either a univalent or a bivalent fragment. Also, to minimize nonspecific reactivity of particle surfaces, such as those of glass or latex, it will be found advantageous to cover these surfaces, either by coating or coupling with non-reactive proteins or other suitable materials.

All of the above known procedures are illustrative of the broad field in which agglutination has been used. The field of usefulness of the methods of the present invention for detecting aggregate classes and measuring agglutination is correspondingly broad, and is not intended to be limited to the particular examples that have been mentioned.

THE PRIOR ART

There are numerous books and probably many hundreds of papers which describe a wide variety of agglutination reactions in general, as well as various modifications. A large proportion of those disclosures concern hemagglutination reactions, which use red blood cells as carrier particles. Detailed procedures for handling many such materials are well described, with numerous references to the original literature, in "Methods in Immunology and Immunochemistry," edited by Curtis A. Williams and Merrill W. Chase, Volume IV, Chapter 16, pages 1 to 125, Academic Press, Inc., 1977, which is cited as useful background material. In most of those procedures detection of agglutination is visual, and determines only which one of a series of dilutions of the test reactant still gives, or does not give, detectable agglutination.

The prior art methods which may be said to "measure" the extent of agglutination have generally treated the suspension as a whole, without any attention to individual aggregates. Typical of such methods are those which measure some property of light transmitted by the suspension or scattered by it at certain angles of measurement. For example, U.S. Pat. No. 4,313,929 to Shiro Morita et al describes the measurement of light intensity or the rate of change of light intensity scattered at a definite angle from the suspension as a whole.

Presence of agglutination has also been demonstrated by measuring the frequency shift of monochromatic light when scattered quasi-elastically by the suspension. The Brownian motion of each suspended body causes a frequency shift that varies statistically within limits that are inversely related to the size of the body. The observed spectral broadening, however, necessarily represents an average over all aggregates and single particles present in the suspension. That method of measurement is described, for example, in U.S. Pat. No. 4,080,264 to Richard J. Cohen et al. Methods for optimizing the process by controlling the size distribution of aggregates are discussed in U.S. Pat. No. 4,164,558 to Gustav K. von Schulthess et al, but without any capability for measuring only a portion of the entire array of aggregate sizes. U.S. Pat. No. 3,984,533 to E. E. Uzgiris uses a generally similar technique for measuring the average electrophoretic mobility of all particles in a suspension.

Agglutination has also been detected indirectly in terms of the resulting decrease in the number of unagglutinated particles in the suspension. For example, a sample may be passed through the flow-cell of an automatic particle counting device which has been modified to count only single particles. That approach is typically described by Daniel Collet-Cassart et al in "Automated Particle-Counting Immunoassay for Digoxin," Clin. Chem. 27/7, 1205–1209 (1981).

A more extensive account of Particle Counting Immunoassay (PACIA) and of illustrative problems to which it and the present invention are both applicable is given in "Immunochemical Techniques (Part C)" edited by John J. Langone and Helen Van Vunakis, which is Volume 74 of "Methods in Enzymology," Academic Press, 1981. That work employs apparatus (see especially pages 106 to 111) which is commercially available from Technicon Corporation of Tarrytown, N.Y. A light beam is focused on a flow-cell and the light scattered through a definite small angle characteristic of single carrier particles is selectively focused on a photo-tube. The resulting light pulses provide a count of single particles passing through the cell.

The suggestion has also been made, in U.S. Pat. No. 4,191,739 to E. E. Uzgiris et al, that the "resistive pulse method" might provide a sensitive method for measuring reactions, since it is capable of responding to aggregates of only two or three beads each. In that method particles are forced by pressure or by electrophoresis through a microscopic orifice between two chambers, momentarily altering an electrical potential applied across the orifice. The patent describes and claims a method for avoiding errors due to autoaggregation during sensitization of the beads. Such errors are avoided by separately sensitizing beads of two different sizes with one reagent, then mixing them together and with the other reagent, and detecting only those complexes which consist of one bead of each size. Such counts exclude any aggregates that may have been formed accidentally during sensitization of beads of either size. That procedure and its specific advantage are clearly distinct from the present invention.

DESCRIPTION OF PREFERRED EMBODIMENTS

Measurement Techniques

To determine the extent of agglutination of a test suspension, for example for assay of the concentration of an analyte, the present invention typically scans a representative field of the suspension in any suitable manner to produce electrical signals representing light intensity at an array of closely spaced elementary positions in the field. Those signals will be referred to as "position signals."

The suspension field may be imaged on a rectangular array of discrete light responsive elements, such as light sensitive diodes, which develop individual signals directly; or a linear array of such elements may be swept transversely relative to the field by optical means of known type, causing each element to scan the field along a distinct path.

The individual position signals developed during a field scan or equivalent operation are typically converted to digital form and recorded in a conventional memory device together with an identification of the field positions to which they correspond. A suitable general purpose digital computer may then be programmed in conventional manner to process the stored data to perform any desired manipulation.

As an illustration of such processing, the computer is programmed to analyze the position signals and their associated position information to detect and measure individual aggregates in the scanned field, and to derive the number of aggregates that belong to at least one previously identified class. Each such class is typically defined by a specified range of values of an aggregate parameter, such as apparent aggregate area, for example.

In brief summary, that signal analysis typically includes such steps as the following: The computer selects from the array of position signals those signals that are associated with carrier particles rather than with field background. The so selected "particles" are formed into groups such that all signals of each group are associated with mutually adjacent positions, and thus represent a distinct object in the field. Each such group of particle signals that represents an individual aggregate is then analysed to determine the value of the class-defining parameter for that aggregate. A "class signal" is developed representing that parameter value. The upper and lower parameter values that define the aggregate class are compared with each such class signal to indicate whether the associated aggregate is a member of the class. A count is made of the number of aggregates found to belong to the class, and the resulting class counts provide a basis for quantifying the extent of agglutination. If the measurement of the extent of agglutination is to be used for assay of the concentration of an analyte taking part in the reaction process, the class counts are compared with standard aggregate counts obtained in corresponding manner by reaction of known standard quantities of analyte to be assayed, as described in following sections of this specification. The illustrative steps of data processing outlined above will now be described more fully.

For example, the computer is programmed to select position signals that are characteristic of carrier particles rather than of the field background. That selection of particle signals will generally be made in terms of the light intensity represented by the signal, and the distinction between particles and background may then be carried out directly on each analogue position signal, effectively reducing it to binary form prior to storing. However, if the particles have a distinctive color each position signal may comprise two or more distinct components representing respective wavelength regions which are separately sensed with the help of conventional beam splitting optics and/or color filters. Discrimination between field signals and particle signals may then be made in terms of the ratio of the color components, for example. Such discrimination can also be made between two or more types of particle having different colors.

The computer is further programmed to compare the positions of the various signals corresponding to particles, and to identify groups of such particle signals that are mutually adjacent with respect to their positions in the field, and are therefore all associated with the same physical object in the suspension. That object may be a single particle, provided the individual particles are large enough to be resolved by the optical system, or may comprise an aggregate of agglutinated particles.

In accordance with that form of the present invention, each group of particle signals associated with an individual aggregate is typically analyzed to determine the value for that aggregate of a parameter which has been selected for discriminating between aggregates that are to be included in the analysis and those that will be disregarded. A signal is developed for each aggregate, using the value of that parameter and representing that parameter value. That signal is distinctive of the selected aggregate class, and will be referred to as the class signal. For clarity of the present description, the selected of that parameter. That signal is distinctive of the selected parameter will generally be assumed to be the apparent area of the aggregate as viewed by the optical scanning apparatus. The class signals then represent the areas of the respective individual aggregates.

If the position signals correspond to uniformly spaced field elements, as is preferred, the apparent area of each object may be determined by counting the number of particle signals in each group. For example, if the signals correspond to positions forming a square grid of one micron spacing, the area of an object can be expressed in square microns by simply counting the number of signals in the associated group.

Alternatively, if the scanning is performed by a video camera or other device which develops continuously variable analogue signals corresponding to successive laterally displaced sweeps across the field, the video signal developed during each sweep may be considered to comprise small elemental sections which are identified by their time relation to the periodic synchronizing time signal that controls the sweeps. Each object in the field may then be associated with certain sweep signal segments that are "adjacent" with respect to both the sweep in which they occur and their time relations to the synchronizing signals. The area of each object can then be expressed as the product of the scan interval by the sum of the lengths of such overlapping sweep portions.

As an alternative approach to processing the signals, the computer may, for example, detect boundaries of field objects directly, as by comparing neighboring signals to find positions where the signals alter abruptly as a function of position. Each object is then defined by the sequence of positions along its boundary, rather than by the signals within its area. The area of an object can then be computed, for example, in terms of differences in the x and y coordinates of boundary points. That approach also facilitates discrimination of particles having distinctive shapes, as by use of well known pattern recognition techniques. It will be understood that other types of scanning devices and processing procedures may be employed, for each of which the area and other desired properties of the object can be computed in an appropriate manner to develop class signals.

Thus, each scan of a suspension field typically leads to a list of numbers each of which represents the apparent area of a distinct object of the field, and is represented by a class signal. Those signals may be directly stored in memory, together with any desired further information about each one. It is generally preferred, however, to provide the computer with at least tentative values of upper and lower limits which define a selected aggregate class, and to program the computer to compare those limits with the class signal for each individual aggregate in the field and determine the number of measured aggregates within the selected class. Those numbers will be referred to as class counts. They are typically stored in memory, and become the primary basis for quantifying the extent of aggregation.

Optical scanning procedures, such as those indicated above, have the advantage that they can be carried out without any disturbance to the incubating suspensions, which are typically contained in conventional small wells, formed in trays which are convenient to handle. The reactants are preferably loaded into the wells automatically in conventional manner. The suspensions are typically stirred intermittently during incubation, and the reaction products are typically measured after a definite settling time and without removing them from the wells. An advantage of optical scanning with electronic recording and processing of the results is that the operating speed can be made sufficient to scan a large number of wells very nearly simultaneously. The scan of each individual field is typically so rapid as to be virtually instantaneous. Successive scans can therefore be timed with excellent accuracy, even when a relatively large number of wells must be treated in strictly comparable manner. So long as the scanned field is typical of the entire well it may be relatively small and still yield results that are accurately representative of the entire suspension.

An alternative approach to measuring the aggregations of particles employs some form of flow cell through which a portion of the suspension fluid is passed, typically along a narrowly confined linear path. Monitoring apparatus is mounted adjacent that path, responsive to passage of each individual particle or aggregate of particles. The monitoring device typically responds selectively to aggregates of different sizes. Only a relatively small portion of the entire suspension needs to be withdrawn to obtain aggregates representative of the whole reaction product.

One well-known form of flow cell uses a sharply focused transverse light beam with a light detector responsive only to light scattered at a certain small angle. Any body crossing the light beam then causes the detector to produce a signal of pulse form, the amplitude of which varies in general accord with the size of the body. Such "particle counters" and accessory equipment are available commercially from Technicon Instruments Corporation of Tarrytown, N.Y. and also from HIAC/ROYCO Instruments division, Pacific Scientific of Menlo Park, Calif., for example.

Another form of particle detector uses a small orifice between two chambers which are connected to different electrical potentials. The resulting field at the orifice is disturbed by passage of a solid body having electrical characteristics different from those of the fluid medium. That disturbance is sensed by electrodes in the chambers, typically producing a potential pulse which varies in amplitude with the size of the body. Apparatus of that general type is available commercially from Particle Data, Inc. of Elmhurst, Ill. Both the electrical and optical forms of flow apparatus give a signal that typically represents particle size, although they tend to reflect different measures of size, corresponding roughly to volume and area, respectively.

The particular aggregate size or sizes selected for measurement may vary greatly with the nature of the reactant substances and of the particles, and with the operating conditions. If the particles to be agglutinated are of a size to be optically visible with suitable magnification, as when blood cells or bacteria are used, for example, even the smallest complexes can be measured and counted in the illustrative manners already described. If the particle diameter is of the order of the wavelength of light, as is usually true of latex beads and the like in conventional practice, the patterns of development of aggregates can start to be measured as soon as their size becomes sufficient. Thus, the invention finds effective application in assaying agglutination of particles of any size that is useful for conventional assays.

For optical measurements the incident radiation as well as the detected radiation may encompass a wide spectral region, from far ultraviolet to near infrared for example, or may be limited in known manner to only a selected range of wavelengths or a single wavelength. Many different optical systems and transducer devices are available for sensing such radiation, and certain of them will be particularly useful for certain applications.

In addition, under certain conditions it will be desirable to use a combination of optical systems, as to sense two or more parameters which relate to different characteristics of the radiation and measure different properties of the aggregates. When that is done, an aggregate class may be defined in terms of both those parameters. For example, if the analyte exhibits fluorescence, then a measure of the total fluorescence intensity for each individual aggregate in the field may provide one class-defining parameter. If the degree of polarization of that radiation is also measured, the resulting values may provide additional information about the state of the fluorescing reactant and may be used to define a further aggregate class. Similarly, the refractive index of each aggregate may be measured along with the intensity of the scattered light, say. When such pairs of parameters are measured for each aggregate the resulting sets of values, singly or in combination, may be used to define class parameters.

An example of a class defined in terms of two parameters would specify the aggregate shape by the ratio of length to width, for example. Another illustrative configurational parameter includes a measure of the openness or opacity of the aggregate structure, such as a ratio of the light reflected by an individual aggregate divided by its apparent geometrical area.

Measurements of the extent of agglutination may be useful for many purposes, such as detection of subtle differences between two generally similar materials. For example, if two samples of the same drug obtained from different sources and reported to be of equal concentrations are subjected to agglutinating reactions under identical conditions, identical extents of agglutination should prevail throughout the reactions. Detection of differences in extent of such agglutination would suggest non-identity of the two materials.

Selection of Aggregate Classes for an Assay

Measurements of agglutination are ordinarily used for determining the concentration of a particular reactant which takes part in the agglutinating process and is originally present in a test solution or suspension. Such assay of a test substance or analyte normally involves measurement of the extent of agglutination due to the test reaction and comparison of the test results with data obtained in corresponding manner with standard reactions using known amounts of standard materials and appropriate controls. A distinctive feature of the present invention is that the extent of agglutination measurements for both the test and standard reactions are limited to measurements of the number of one or more specific classes of aggregates. Thus, an important aspect of the invention concerns the selection of suitable classes of aggregates to be taken into account in assaying particular substances.

The factors affecting that selection of aggregate classes can be better understood by consideration of the dynamics of aggregate formation and growth, which directly influence the distribution of aggregates among the illustrative group of aggregate classes defined in terms of aggregate size.

When a solution containing one reactant is combined with a suspension of particles sensitized with the complementary reactant, the first aggregates to be formed contain only two particles, linked by a multivalent molecule of the dissblved reactant. As incubation proceeds, the number of such dual aggregates in the suspension increases and the single particles decrease in number. A remaining single particle therefore becomes progressively more likely to combine with an existing dual aggregate rather than with another single particle. Hence the net rate of production of dual aggregates decreases and the rate of growth of triplets increases. Similarly, quadruplets and larger aggregates tend to appear in turn. Under suitable conditions, including the nature and initial concentrations of the reactants and the size and degree of sensitization of the particles, many individual aggregates may continue to grow till they reach several tens or hundreds of particles each. As the average of all aggregate sizes increases with time, the number in any size interval tends to increase more and more slowly, and then to pass through a maximum and decrease. The patterns of development for relatively small sizes increase relatively rapidly, pass through a relatively sharp maximum, and tend to decrease considerably from their maximum values. For the largest aggregates, the number in a limited size interval is typically still growing slowly as the reaction approaches equilibrium. This description is somewhat simplified for the sake of clarity, omitting, for example, such factors as affinities of reactants and the tendency for the most probable aggregate to dominate as a statistical process.

The patterns of development of different aggregate classes depend significantly upon many experimental conditions, and especially upon the particular reagents and their concentrations. Hence, to obtain optimum advantage from the invention it is preferred to select aggregate classes to be measured in coordination with the choice of time or times for the measurement of each class, and with close attention to the particular substance to be assayed and its probable concentration in the test solution or suspension.

In normal practice the selection of a suitable aggregate class for any particular assay will ordinarily be based largely on previous experience with the same reagents and with similar operational conditions. In absence of such experience, the interrelations of parameter values for the reagents in question are explored experimentally, and especially favorable aggregate classes are selected on the basis of the resulting data.

To carry out preliminary measurements for assay of an antigen in solution, say, various known standard quantities of the antigen are reacted with aliquots of a complementary antibody bound on insoluble particles. Other conditions are held strictly uniform for all reactions of the set, and correspond to the conditions that will be used for the actual assay. Aggregates due to each of those reactions are measured with respect to whatever parameter is considered to define a potentially useful aggregate class. Thus, to explore aggregate sizes as a possible class definition, the size of each observed aggregate is measured, all measurements of a set being made at substantially the same time. Measurements at other times will be discussed later.

From the resulting set of data a graph is typically drawn for each initial antigen concentration, showing the number of aggregates as a function of aggregate size. Those size distribution curves contain the basic information in convenient form, inspection of which indicates aggregate size intervals capable of forming useful aggregate classes. Class selection may also be aided by plotting for each such size interval a graph showing the number of aggregates having sizes within that size interval as a function of initial antigen concentration.

Many of the graphs of aggregate count vs. antigen concentration will be found to include portions having a relatively steep slope, distinctly steeper than the average slope, say. Such portions indicate ranges of the antigen concentration that are represented especially sensitively by aggregate counts for the size interval of the particular graph. Hence that aggregate size interval is indicated to be a favorable parameter for assay of the antigen in that particular concentration range. For some purposes, that level of analysis may be a sufficient basis for final selection of an aggregate class for the assay.

The interrelationships of a set of reference data, as so far described, can often be more clearly visualized by programming the computer to plot a three-dimensional graph which shows aggregate size and initial analyte concentration plotted on the x and y axes, say, and the corresponding numbers of aggregates plotted along the z axis. Such a graph shows clearly the most sensitive aggregate size for any range of analyte concentration, for example, and indicates how many sizes should be measured to cover with good sensitivity the full range of concentrations anticipated in a particular assay. In some cases, especially for assays of a routine nature, measurement and processing of aggregates within a single size interval may give excellent accuracy throughout the anticipated range of concentrations.

The preceding discussion of class selection has been limited for the sake of clarity to measurement of the reference reactions at a single time. To take advantage of the time parameter, additional sets of measurements are made at a series of times, extending over a time range which may be selected with the aid of preliminary tests. The reaction parameters are measured and the resulting numbers of aggregates are processed in the manner already described, preferably for the same size intervals as before, leading to similar sets of graphs showing aggregate counts vs. standard analyte concentration for each time. A three-dimensional graph is preferably prepared for each time of measurement.

Intercomparison of the latter graphs typically shows that the most favorable aggregate size for one time differs from that for another time. Moreover, for a given size, the most sensitive relation typically occurs for one analyte concentration at one time and for another concentration at another time. It will often be possible, however, to find a single aggregate size that gives good sensitivity throughout the desired concentration range by measuring at one time for part of that range and at another time for another part. Sometimes each portion of the concentration range is best covered by a particular size and a particular time of measurement appropriate to that size. Alternatively, analysis of the data will sometimes indicate a particularly favorable range of concentrations of the analyte, for which a particularly favorable aggregate class is available. The anticipated analyte concentration in a test solution can often be brought into that favorable range by suitable dilution of the original test medium.

The process of class selection has been described largely in terms of plotting and inspecting graphs in order to make clear the principles of the method. It is well known how to translate such operations for computer processing, using correlation coefficients, method of least squares and the like.

Especially when class selection is found to involve significant compromise between approaches that are not fully compatible, a satisfactory solution can often be found most conveniently by using conventional techniques of multivariate analysis. Computer programs are readily available for reaching a compromise among available criteria, typically leading to a set of class definitions that meets prescribed conditions.

It is emphasized, however, that a very significant gain is attainable over the prior art without absolute optimization of the sensitivity of the selected class or classes. The selection process can involve many compromises and still insure an assay based on measurement of a parameter that responds far more favorably to the variable being determined than any mere summation of all aggregates.

Following such initial explorations with a particular antigen and antibody, say, routine assays with those same substances can usually be confined to measurements of a relatively small number of aggregate sizes and times of measurement. In fact, in many cases the parameter values finally selected may include only a single size interval and a single time of measurement, the coordinated values of which have been chosen in the light of relatively extensive preliminary data. Such a narrowly defined set of parameters, since it has been selected expressly to provide a highly sensitive reflection of the desired initial reactant concentration, typically yields a more accurate and reliable quantitative assay than could be obtained in the prior art by measuring aggregates of all sizes lumped together.

Although the preceding description has been expressed for clarity mainly in terms of classes defined by aggregate size, it will be understood that relationships of other parameters or sets of parameters or combinations of various parameters can be explored in similar manner, leading to identification of favorable aggregate classes defined by selected value ranges of those parameters. Such parameters may relate to substantially any property that is measurable for individual aggregates, such as specific dimensions, light absorbance or scattering, density or electrical properties.

Measurements of several distinct aggregate parameters at multiple times makes available a wide variety of aggregate classes, from which one or several may be selected for actual comparison between test and standard results. When several such classes are selected for measurement, the computer is typically programmed to process the test results for each class independently of the others, leading to separate though not necessarily independent assay values for the analyte concentration. Those values are then typically averaged with appropriate weighting, yielding an overall result of enhanced accuracy and reliability.

Also, aggregate classes may be defined in terms of specific functions of several distinct parameters, or functions of distinct values of a single parameter measured at different times, for example. When such a class is selected, measured parameter values are processed to compute a test value of the function, obtained with the test analyte, which is then compared with suitable standard values of that same function, obtained from measurements with the appropriate standards. For example, measurements of a parameter at a series of times following the start of the test reaction are processed to derive the rate of change of that parameter. A selected range of the values of that rate of change then defines an aggregate class, which may be used as a measure of analyte concentration.

Results of such parameter measurements and/or function derivations for different times can be interpolated to a convenient time, or can be extrapolated to a time beyond the range of actual measurement, for example to zero or other early time, or to effectively infinite time after which no further significant changes occur. As a further example of class-defining functions, an aggregate class may be defined by a certain range of values of the ratio of two distinct parameters, such as the measured maximum and minimum diameters of each aggregate. The number of aggregates for which the computed value of such a derived test parameter is within the class-defining interval is compared with the corresponding numbers of aggregates obtained from sets of standard values of the same function derived in corresponding manner from reactions with known standard quantities of the analyte.

A further useful benefit of the above described computer exploration of reference reactions is that operating conditions can be identified under which certain ranges of the aggregate count or other class value are found to occur only rarely or not at all. Such information provides a check on correct operation of the system: during regular test runs the computer is programmed to monitor the counts for occurrence of any rare class values, and to produce a signal indicating possible malfunction.

When quantitating an analyte, it will often be found useful to include redundancy in the aggregate classes that are selected for the assay. In particular, if satisfactory sensitivity for the conditions at hand, including a particular range of anticipated analyte concentrations, is found to be presented by a certain interval of a class-defining parameter, it is often helpful to select not only the class defined by that interval but also some classes which show maximum sensitivity for a lower range of analyte concentration and some which show maximum sensitivity for a higher range of analyte concentration. By extending the measurements and computations to include such redundant classes, the extent of aggregation at the lower and higher ranges of analyte concentration are taken into account and may allow for more accurate description of the extent of aggregation and hence of quantitation of the analyte than when such information is not used.

Reference Standards for Assays

The production and use of comparison standards in connection with the present invention are not fundamentally different from those already familiar in many types of biological assays. However, the following comments may clarify certain points and avoid misunderstanding.

An illustrative problem is to assay a test solution for the concentration of an antigen, say, which is also available at known concentration in a standard solution, and for which a specific antibody is available bound on particles of latex or other suitable material. Aliquots of the antibody suspension are typically reacted with one or more concentrations of the test solution to produce test suspensions; and further such aliquots of antibody suspension are reacted with standard solutions containing a series of known concentrations of the standard antigen to produce standard suspensions. The suspensions are all incubated and then scanned or otherwise measured in corresponding time relation to the start of incubation. The resulting signals from test and standard suspensions are processed in corresponding manner to give test and standard values. By "corresponding" is meant that all conditions except those purposely varied are as nearly equal or equivalent as is feasible. Those conditions include mixing and time of measurement, as well as such factors as particle size, pH, salt concentration, temperature and possible presence of other substances in the fluid. The latter factor may also require the inclusion of further specific controls.

Under such corresponding conditions the result is a set of directly comparable test and standard values of one or more aggregate parameters distinctive of whatever class or classes have been selected for measurement and comparison. From those measured parameter values are derived the numbers of aggregates of each selected class. Those aggregate counts constitute the basic information for describing the extent of agglutination and allow quantification of the analyte.

The number of aggregates of each selected class for the test reactions can be compared directly with the corresponding numbers for the standard reactions; or an effective comparison can be made in terms of any suitable function for which values are derivable from the parameter values. For example, such a function would be the time rate of change of the number of aggregates of a particular class, and would be compared with the time rates of change of corresponding standard numbers of aggregates as a measure of analyte concentration. The function may depend also upon other parameters, so long as the latter are kept effectively constant for both test and standard reactions, or their variation is properly taken into account in the computations. Such a function may be viewed either as a means for comparing the original parameter values or as a derived parameter which is compared directly. Reference in the appended claims to comparison of test and standard values of numbers of aggregates of a selected size, for example, is intended to embrace comparison of any suitable function of such numbers as well as comparison of the numbers themselves.

The actual comparison of the test values with the standard values may be carried out in any suitable manner, and need not be described here in detail. In its simplest form, one would plot the standard values of the selected parameter or parameters as functions of the quantity of the substance to be assayed, and find the point on such curves which match the test data.

The standard curves used in that standardizing operation are similar to certain of the reference graphs of aggregate parameters vs. analyte concentration which have been described for aggregate class selection. In fact, both may sometimes be derived from the same reactions. However, a more extensive variety of analyte concentrations and measurements is usually required for class selections, and the standardizing curves are preferably developed from reactions run in parallel with the actual test reactions. Therefore, in practice distinct reactions and distinct curves are ordinarily used for the two purposes.

When the test substance to be assayed is initially present in solution, the result of the assay is ordinarily expressed as the initial concentration of analyte in the test solution, which may be stated in any convenient units such as moles or micrograms per unit volume of solution. When the test substance is initially present on surfaces of the particles that become agglutinated due to the reaction, the quantity of test substance as determined by assay may be expressed in any form that is available for defining the quantity of substance present in the standard suspensions employed for standardizing the assay.

Thus, if standard suspensions are available which contain a known quantity of the test reactant per unit number of particles or per unit mass of particles, for example, or per unit volume of suspension, then the assay results will usually be most conveniently expressed in corresponding units. A property of natural cells, such as an antigenic site on the cell surface, can be quantitated in terms of an effective concentration of a standard antiserum or, if the antibody is coupled to particles as described above in the section "Outline of the Invention," in terms of the standard suspension of the so sensitized particles.

For assay by indirect agglutination and by inhibition of agglutination, in which at least three distinct species of reactant are typically involved, the test results are compared with standard values obtained in corresponding manner with standard quantities of all three species, using several different quantities of at least the substance to be assayed.

In accordance with another aspect of the invention, a solution can be analyzed for a reactant with improved sensitivity by measuring the effect of the reactant in enhancing agglutination. For example, a test solution may be analyzed for antigen, say, by reacting a definite amount of a suspension of particles carrying the complementary antibody with a sample of the test solution and also with a definite amount of the antigen in solution sufficient to produce slight but measurable reference aggregation when reacted with such particle suspension directly. Any antigen in the test solution will increase the total amount of antigen available to produce agglutination, and, under appropriate conditions, will enhance the reference agglutination by a relatively high percentage. If the overall agglutination is then measured by the improved assay process that has been described, proper selection of aggregate class for that assay may further improve the sensitivity of the determination.

A further aspect of the invention makes use of the fact that many analytes exhibit at least two independent antigenic sites (epitopes). Work of preparing antibodies against specific binding sites is now well known, and some of this work has recently been reviewed by J. G. Sutcliffe et al in Science, 219, 660, 1983. The current technology for specifically assaying such substances employs radioactively labeled materials as tracers.

The present invention permits assay of these multi-site analytes by a new form of indirect agglutination, which has the significant advantage of avoiding the use of radioactive materials, while retaining the full specificity made possible by use of dual independent sites.

In illustrative form of the invention, antibody, such as monoclonal antibody against one specific site of the analyte is coupled to suitable insoluble particles. Test analyte is added, and will bind to the particle-bound antibody, but usually without producing agglutination. The reaction is best carried out in antibody excess.

A second antibody, specific to the analyte at a second site, is then added, and may result in agglutination. If aggregation occurs then it is quantitated, preferably as described in this disclosure. If aggregation does not occur at that step, agglutination is produced by addition of anti-antibody with specificity against the second antibody.

The resulting agglutination, whether due to the second antibody or to the anti-antibody, is quantitated, preferably by the improved assay process that has been described, and is compared with correspondingly prepared standards to determine the initial concentration of analyte in the test solution.

Thus, the present aspect of the invention provides a quantitative agglutination assay for more reliable identification of the test substance than was previously available, since it involves dual specificity at the two independent reaction sites of the test molecule. The use of the quantitative agglutination assay constitutes a significant advantage over currently used radioimmunoassay methods because it obviates the frequently undesirable use of radioactive materials.

We claim:

1. The method for assaying the extent of particle agglutination due to reaction of a first substance present on insoluble carrier particles and a complementary second substnace, comprising identifying, for particle aggregate due to reaction of said substances, at least one limited class of aggregate for which the aggregate count or counts reflect espacially sensitively the overall extent of agglutination, measuring individual particle aggregates due to the reaction to be assayed to develop for each measured aggregate electrical class signals distinctive of said class or classes, processing the signals to derive the number of aggregate of each identified class, and using the resulting number or numbers as a measure of the extent of agglutination.

2. The method according to claim 1 wherein a said class is defined by a limited range of an aggregate parameters, and said signals represent values of such parameter or parameters.

3. The method according to claim 1 wherein a said class is defined by a limited range of a parameter that represents a measure of the aggregate configuration, and said signals represent values of such parameter.

4. The method according to claim 1 wherein a said class is defined by a limited range of a parameter that represents a measure of the aggregate size, and said signals represent values of such parameter.

5. The method according to claim 1 wherein said measurement of particle aggregates comprises automatically scanning an optical field containing representative aggregates to produce electrical signals that correspond to respective field elements, and discriminating particle signals that correspond to field elements occupied by particles, identifying groups of particle signals such that all signals of each group are associated with the same aggregate, and developing from each signal group a class signal distinctive of an identified aggregate class.

6. The method according to claim 1 wherein said measurement of particle aggregates comprises passing a portion of the aggregate suspension through a confined region and developing a class signal responsive to each aggregate passing through the region and distinctive of an identified aggregate class.

7. The method according to claim 1 wherein said measurement of particle aggregation is carried out at each of a plurality of times, and said class signals are processed to derive the number of aggregates of each identified class at each of said measurement times.

8. The method according to claim 1 wherein said measurement of particle aggregates is carried out at each of a plurality of times, and said class signals are processed to derive the time rate of change of the number of aggregates of each identified class as a measure of the extent of agglutination.

9. The method according to claim 1 wherein said measurement of aggregates is carried out after said reaction has reached substantial equilibrium.

10. The method according to claim 1 wherein one of said substances is an antigen and the other said substance is an antibody specific to the antigen.

11. The method according to claim 1 wherein one of said substances is a carbohydrate and the other said substance is a lectin complementary to the carbohydrate.

12. The method according to claim 1 wherein one of said substances is a receptor specifically present on natural cells or coupled to artificial particles, and the other said substance is a ligand specifically reactive with the receptor.

13. The method according to claim 1 wherein the particles carrying said first substance are natural cells, and both said substances are present on insoluble particles.

14. The method according to claim 1 wherein one of said substances is a test substance initially present in a liquid medium to be assayed for the concentration of such substance, said step of aggregate class identification including reacting different known quantities of the test substance with aliquots of the other substance, measuring individual particle aggregates for each of those reactions, and processing the measurements to identify one or more sensitive aggregate classes for which the number of aggregates in the class depends relatively sensitively upon the quantity of test substance in said liquid medium, and selecting at least one so identified aggregate class for assay of the extent of agglutination.

15. The method according to claim 14 including measuring said particle aggregates at a plurality of times, processing the measurements to identify at least one sensitive aggregate class for each time of measurement, and selecting at least one so identified class and associated time of measurement for assay of the extent of agglutination.

16. The method according to claim 1 wherein reaction of said first and second substances binds them together substantially without agglutination of said carrier particles, and said method includes contacting the resulting reaction product with a further substance complementary to said second substance to produce said particle agglutination.

17. The method according to claim 16 including isolating said reaction product from nonreactive components prior to contacting with said further substance.

18. The method for assaying a test substance which is specifically reactive with a complementary substance to cause aggregation of insoluble particles, one of said substances being present on the particle surfaces, said method comprising reacting the complementary substance with the test substance to produce aggregation of associated particles, measuring individual aggregates due to such reaction to determine the number of aggregates of at least one selected limited class, and comparing the so determined number of aggregates with standard aggregate numbers, which are obtained in corresponding manner by reaction of known standard quantities of said substances, to determine the quantity of said test substance.

19. The method according to claim 18 wherein the method for obtaining said standard aggregate numbers includes reacting different known quantities of a standard of the test substance with aliquots of said complementary substance to produce aggregation of particles upon surfaces of which said one substance is present.

and measuring aggregates due to such reactions, in a manner corresponding to claim 18, to determine for each such reaction the number of aggregates of said selected class.

20. The method according to claim 18 wherein said selected aggregate class is such that the number of aggregates in the class is a relatively sensitive function of the quantity of said test substance.

21. The method according to claim 18 wherein said measurement of aggregates includes determination of the number of aggregates in each of a plurality of distinct classes such that the numbers for at least two such classes are sensitive functions of the quantity of said test substance for respective different ranges of that quantity.

22. The method according to claim 18 wherein said selected aggregate class comprises aggregates having sizes within a limited size interval such that the number of aggregates in the class is a relatively sensitive function of the quantity of said test substance.

23. The method according to claim 18 wherein
said measurement of aggregates includes determination of the number of aggregates having sizes within each of a plurality of distinct selected size intervals,
and the resulting number of aggregates for each size interval is compared with corresponding standard aggregate numbers for that size interval to determine a value of the quantity of test substance.

24. The method according to claim 18 wherein said measurement of aggregates includes measurements at a plurality of times.

25. The method according to claim 18 wherein
said measurement of aggregates includes measurements at a plurality of times, and the resulting numbers of aggregates for the respective times are interpolated or extrapolated to some convenient time or are extrapolated to effectively infinite time at which no further significant changes occur,
and said comparison of aggregate numbers is made in terms of the resulting interpolated or extrapolated value of aggregate number, which is compared with corresponding values of aggregate numbers, obtained by reaction of standard quantities of the substances, to determine a value for the quantity of the test substance.

26. The method according to claim 18 wherein
said measurement of aggregates includes measurements at a plurality of times and derivation of the rate of change of the number of aggregates of a selected limited class,
and said comparison of aggregate numbers is made in terms of the resulting rate of change value, which is compared with corresponding standard rate of change values, obtained by reaction of standard quantities of the substances, to determine a value for the quantity of the test substance.

27. The method according to claim 18 wherein said test substance is a protein or other immunochemically reactive material, and the complementary substance is antibody specifically reactive with the test substance.

28. A method according to claim 18 wherein said test substance is antibody against said complementary substance, and said complementary substance is a known antigen which is present on known natural cells or coupled to artificial particles, as for the detection and quantitation of antibody.

29. The method according to claim 18 wherein said test substance is an antigen or antigenic site present on the cell surface of natural cells, and the complementary substance is antibody of known specificity against the cellular antigen, as for quantitative typing of red blood cells, white blood cells, microorganisms or other natural cells.

30. The method according to claim 29 wherein said antibody is present on insoluble particles.

31. The method according to claim 18 wherein said test substance is a protein or ligand, and the complementary substance is a receptor specifically reactive with the test substance and specifically present on natural cells or coupled to artificial particles.

32. The method according to claim 18 wherein said test substance is a lectin and the other substance is a carbohydrate present on natural cells.

33. The method according to claim 18 including
reacting different known quantities of a standard of the test substance and aliquots of said complementary substance to produce aggregation of said particles,
measuring the distribution of the resulting aggregates with respect to one or more selected aggregate parameters,
processing the resulting distributions to identify one or more sensitive intervals of said parameters for which the number of aggregates depends relatively sensitively upon the initial quantity of the test substance,
and selecting at least one such sensitive parameter interval for defining said selected limited class.

34. The method according to claim 33 wherein said selected aggregate parameter is a measure of aggregate size, said aggregate distributions are aggregate size distributions, said selected parameter interval is a size interval and said aggregate class comprises aggregates having sizes within that size interval.

35. The method according to claim 33 wherein said aggregate distributions are measured at each of a plurality of times.

36. The method according to claim 35 wherein said aggregate distributions are processed to identify a measurement time for which the number of aggregates of said selected class is relatively stable with respect to time.

37. The method according to claim 35 wherein said aggregate distributions are processed to identify a measurement time and an associated value interval of said parameter for which the number of aggregates in said class is relatively responsive to variations in the initial quantity of test substance.

38. The method according to claim 37 wherein said selected aggregate parameter is a measure of aggregate size.

39. The method according to claim 33 including
identifying at least one sensitive parameter interval for each of said quantities of test substance,
and selecting for said assay at least one parameter interval that is sensitive substantially throughout the anticipated range of quantities of the test substance under assay.

40. The method according to claim 18 wherein reaction of said test and complementary substances binds them together substantially without agglutination of said carrier particles, and said method includes contacting the resulting reaction product with a further substance complementary to said complementary substance to produce said particle aggregation.

41. The method according to claim 40 including isolating said reaction product from nonreactive components prior to contacting with said further substance.

42. The method according to claim 40 wherein said test substance is an antigen or antigenic site present on natural cells, said complementary substance, is an antibody specific to the test substance, and said further substance is an anti-antibody specific to said antibody.

43. The method according to claim 40 wherein said test substance is a carbohydrate present on natural cells, said complementary substance is a lectin specific the test substance, and said further substance is an antibody against the lectin or a carbohydrate moiety reactive with the lectin.

44. The method according to claim 40 wherein said test substance is an antibody which does not cause agglutination in the reaction mixture, said complementary substance is an antigen or antigenic site present on natural cells or bound to artificial particles and specifically reactive with the test substance, and said further substance is anti-antibody.

45. The method according to claim 40 wherein said test substance is a receptor on natural cells or coupled to artificial particles, said complementary substance is a ligand specific to the receptor, and said further substance is a receptor, anti-ligand antibody or a lectin specifically reactive with the ligand.

46. The method according to claim 40 wherein said test substance is an antibody on natural cells or coupled to artificial particles, said complementary substance is an antigen or ligand specific to the test antibody, and said further substance is an antibody against the antigen or ligand.

47. The method according to claim 40 wherein said class is defined by a limited range of a parameter that represents a measure of the aggregate size.

48. The method according to claim 40 wherein said test substance is reacted with antibody which is coupled to said particles and is present in antibody excess, and, after completion of such reaction, the reaction product is contacted with dissolved antibody against the test substance to produce particle aggregation.

49. The method for assaying by inhibition of particle agglutination a test solution for the quantity therein of a test substance which is specifically reactive with a dissolved complementary substance, comprising contacting a portion of said test solution and a limited amount of said complementary substance to bind molecules of said substances together, contacting the resulting reaction with test substance that has been coupled with insoluble particles to cause agglutination of said particles due to reaction of the so coupled test substance and the unreacted complementary substance, measuring aggregates due to such agglutination to determine the number of aggregates of a selected limited class, and comparing the so determined number of aggregates with standard aggregate numbers, obtained in corresponding manner by like reactions of known standard quantities of said substances, to determine the quantity of test substance in said test solution.

50. The method according to claim 49 wherein said test substance is a drug, ligand or hormone, and said complementary substance is an antibody or receptor specific to the test substance.

51. The method for assaying by enhancement of particle agglutination a test substance which is specifically reactive with a complementary substance, comprising reacting a definite amount of a suspension of said complementary substance bound to insoluble particles with a sample of the test substance, and with a definite amount of additional test substance sufficient to produce a slight but measurable agglutination if reacted directly with said amount of said suspension, measuring the extent of agglutination due to such reaction, wherein said agglutination measurement comprises measuring the resulting aggregates to determine the number of aggregates of a selected limited class for which the number of aggregates of such class reflects especially sensivitely the qunatity of said test substance, and comparing the result with standard results of corresponding measurements of the extent of agglutination due to corresponding reaction of standard quantities of said substances, to determine the initial qunatity of said test substance.

52. The method for assaying by indirect agglutination a dissolved test substance which is specifically reactive with at least two different antibodies, comprising reacting test substance with a first antibody bound to insoluble particles, reacting the resulting reaction product with dissolved second antiobody, and quantitating the resulting agglutination as a measure of the initial concentration of said test substance, wherein said quantitation comprises measuring the resulting aggregates to determine the number of aggregates of a selected class for which the number of aggregates of such class reflects especially sensitively the concentration of said test substance.

53. The method according to claim 52 including, prior to said qunatitation of agglutination, causing the reaction product of the second said reaction to react with antibody with specifically against the second antibody.

* * * * *